(12) United States Patent
Mueller et al.

(10) Patent No.: US 9,087,504 B2
(45) Date of Patent: Jul. 21, 2015

(54) ULTRASONIC TRANSDUCER FOR USE IN A FLUID MEDIUM

(75) Inventors: Roland Mueller, Steinheim (DE); Gerhard Hueftle, Aspach (DE); Michael Horstbrink, Stuttgart-Feuerbach (DE); Tobias Lang, Stuttgart (DE); Sami Radwan, Stuttgart (DE); Bernd Kuenzl, Schwieberdingen (DE); Roland Wanja, Markgroeningen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 487 days.

(21) Appl. No.: 13/502,716

(22) PCT Filed: Sep. 10, 2010

(86) PCT No.: PCT/EP2010/063294
§ 371 (c)(1), (2), (4) Date: Jul. 13, 2012

(87) PCT Pub. No.: WO2011/051042
PCT Pub. Date: May 5, 2011

(65) Prior Publication Data
US 2012/0266677 A1 Oct. 25, 2012

(30) Foreign Application Priority Data
Oct. 29, 2009 (DE) .......................... 10 2009 046 148

(51) Int. Cl.
*G10K 9/122* (2006.01)
*G01N 29/24* (2006.01)
(Continued)

(52) U.S. Cl.
CPC .............. *G10K 9/122* (2013.01); *G01F 23/296* (2013.01); *G01F 23/2968* (2013.01); *G01N 29/2437* (2013.01); *G10K 9/22* (2013.01); *Y10T 29/49005* (2015.01)

(58) Field of Classification Search
CPC ...... G01F 23/296; G01F 1/662; G10K 11/004; G01P 5/24; G01N 29/2437
USPC ............ 73/632; 310/322, 326, 334, 336, 327, 310/337, 340
See application file for complete search history.

(56) References Cited

U.S. PATENT DOCUMENTS 3,821,834 A * 7/1974 McElroy ...................... 29/25.35
6,268,683 B1 7/2001 Li
(Continued)

FOREIGN PATENT DOCUMENTS

DE 44 43 415 6/1996
DE 100 55 893 5/2002
(Continued)

OTHER PUBLICATIONS

International Search Report for PCT/EP2010/063294, dated Dec. 27, 2010.

*Primary Examiner* — Laura Martin
*Assistant Examiner* — Rose M Miller
(74) *Attorney, Agent, or Firm* — Kenyon & Kenyon LLP

(57) ABSTRACT

An ultrasonic transducer for use in a fluid medium includes at least one transducer core having at least one electroacoustic transducer element, and further includes at least one housing having at least two housing parts. At least one first housing part at least partially encloses the transducer core such that a rear side of the electroacoustic transducer element which faces away from the fluid medium is accessible. Furthermore, at least one second housing part is connected to the first housing part. The ultrasonic transducer is essentially terminated by the second housing part on its side, which faces away from the fluid medium.

10 Claims, 2 Drawing Sheets

(51) Int. Cl.
  *G01F 23/296* (2006.01)
  *G10K 9/22* (2006.01)

(56) References Cited

U.S. PATENT DOCUMENTS

| | | | |
|---|---|---|---|
| 7,398,687 B2 * | 7/2008 | Nakajima et al. | 73/661 |
| 2008/0184802 A1 * | 8/2008 | Sato | 73/632 |
| 2008/0218030 A1 | 9/2008 | Asada | |

FOREIGN PATENT DOCUMENTS

| | | |
|---|---|---|
| DE | 10 2007 037 088 | 2/2009 |
| DE | 10 2008 055 126 | 7/2010 |
| FR | 2462837 | 2/1981 |
| JP | 2001-50940 | 2/2001 |
| JP | 2003-302384 | 10/2003 |
| KR | 20090022290 | 3/2009 |
| RU | 1772724 | 10/1992 |
| WO | WO 96/18181 | 6/1996 |

* cited by examiner

ULTRASONIC TRANSDUCER FOR USE IN A FLUID MEDIUM

BACKGROUND OF THE INVENTION

1. Field of the Invention

The present invention relates to an ultrasonic transducer for use in a fluid medium.

2. Description of Related Art

Ultrasonic transducers are known in various fields of use from the related art. For example, ultrasonic transducers are used in automotive engineering in ultrasonic flow meters, for example, in the exhaust system and/or in the intake system of internal combustion engines. Examples of such ultrasonic transducers are described in published German patent application document DE 10 2007 037 088 A1 or German Patent Application DE 10 2008 055 126.0 of the applicant (which is not believed to be prior art). Ultrasonic flow meters are based in many cases on two ultrasonic transducers, which are situated offset in a flow tube in the flow direction and mutually send one another ultrasonic signals. Measuring systems may also be used in which at least one reflector is provided, for example, in the form of plug-in sensors. Further applications of ultrasonic transducers are, for example, filling-level meters or distance meters, for example, in so-called Park Pilot systems.

In many cases, ultrasonic transducers have an electroacoustic transducer element in the form of a piezoceramic. In order to achieve an impedance adjustment, i.e., in particular a reduction of reflection losses at the interface between the ultrasonic transducer and the fluid medium in which the ultrasonic transducer is to be used, in many cases so-called adjusting bodies are used, which ensure at least partial impedance compensation between the piezoceramic and the impedance of the fluid medium. For example, ultrasonic transducers based on a piezoceramic in conjunction with so-called $\lambda/4$ impedance adjustment layers are known. Examples of such adjusting bodies, which may also be used in the scope of the present invention, are described in published German patent application document DE 10 2007 037 088 A1 or German patent application DE 10 2008 055 126.0.

Furthermore, ultrasonic transducers having a housing in the form of a one-piece sleeve and a ring-shaped rear cover are known from the related art. Such ultrasonic transducers are used, for example, in Park Pilot systems. In this case, the piezoceramic is typically first electrically contacted in that, for example, wires are welded to the piezoceramic and to the contact pin connected to the cover ring. Subsequently, the piezoceramic is then typically held with the aid of a vacuum pad gripper through the cover ring and inserted into the sleeve jointly with the cover ring and the connecting wires. During this procedure, the connecting wires receive the bending shape which is desired inside the later ultrasonic transducer for the purpose of ideal durability. Before the vacuum pad gripper may be removed, an adhesive must typically be activated between the piezo and the sleeve, which occurs in many cases in the form of ultraviolet radiation, which is typically also introduced through the cover ring.

In practice, this type of assembly is, however, associated with various technical requirements and disadvantages in practice. Thus, one-piece transducer sleeves must typically be implemented as very deep, because an interior of the transducer sleeves must be filled up with a specific quantity of damping material. Furthermore, this depth of the transducer sleeve is typically required to allow fastening of contact pins or re-contacting in order to ensure an appropriate guide length for a precisely aligned installation, for example, in a plug-in sensor housing, or to make the general handling of the entire transducer easier. However, the handling during the construction process is typically made more difficult by this depth of the transducer sleeve, because the piezoelement must be sunk deep into the transducer sleeve. Electrical contacting of the piezoceramic which is suitable for mass production is then only possible with difficulty inside the sleeve. In contrast, if the electrical contacting of the piezoceramic is performed before the joining with the optional adjusting body, the piezoceramic, the connecting wires, the contact pins, and optionally the transducer cover or transducer cover ring must remain fixed or positioned relative to one another in the scope of the joining procedure. Such a method is extraordinarily complex.

BRIEF SUMMARY OF THE INVENTION

Therefore, an ultrasonic transducer for use in a fluid medium and a method for manufacturing an ultrasonic transducer for use in a fluid medium are proposed, which at least partially avoid the disadvantages of known ultrasonic transducers and manufacturing methods. The ultrasonic transducer may in particular be manufactured as per a method according to the present invention, and the method may in particular be used to manufacture an ultrasonic transducer according to the present invention. Reference may accordingly be made to the description of the ultrasonic transducer for possible embodiments of the method and vice versa.

The present ultrasonic transducer includes at least one transducer core having at least one electroacoustic transducer element. An electroacoustic transducer element is to be understood as a fundamentally arbitrary element which may convert electrical signals into acoustic signals and vice versa. In particular, this may be a monolithic element. The electroacoustic transducer element preferably includes a piezoelectric transducer element or is implemented as a piezoelectric transducer element. Accordingly, in the scope of the present invention, without restriction of other possible embodiments of the electroacoustic transducer element, the terms "piezo," "piezoceramic," and "piezoelectric transducer element" are also used as synonyms for the term "electroacoustic transducer element." In addition, the transducer core may include other elements as explained in greater detail below. For example, the transducer core may include at least one adjusting body on a side which faces toward the fluid medium, for example, according to the above-described related art. This adjusting body is configured to improve an acoustic coupling between the electroacoustic transducer element and the fluid medium, for example, air or a liquid. Ideally, the adjusting body provides a material whose impedance is the geometric mean value of the impedances of the electroacoustic transducer element and the fluid medium. In the real ultrasonic transducer and in particular in the case of a gaseous fluid medium, an adjusting body having a different, typically higher acoustic impedance will typically be used. The adjusting body may also include multiple materials having different acoustic impedances and/or a material having an acoustic impedance gradient. For example, the transducer core may have an emission surface, which faces toward the fluid medium and via which ultrasonic signals may be delivered to the fluid medium and/or ultrasonic signals may be absorbed from the fluid medium. The emission surface may be situated, for example, in an opening of a housing, which will be explained in greater detail below. For example, this opening may be surrounded by an edge of the housing, for example, in a ring-shaped manner. Other geometries are also conceivable. The emission surface may be aligned flush with the edge of the housing or may also be situated in another plane, for example, slightly offset into the interior of the housing or slightly offset in relation to the edge toward the fluid medium.

Furthermore, the ultrasonic transducer includes at least one housing. This housing may be implemented as sleeve-shaped in particular. A housing is understood as an element which terminates the ultrasonic transducer essentially at the outside and gives the ultrasonic transducer its essential shape at the outside. The housing, as explained in greater detail below, may in particular be manufactured from a metallic material and/or a plastic material and may protect the ultrasonic transducer against external mechanical and/or chemical influences and/or against temperature and/or pressure influences.

One idea of the present invention is that the assembly and the construction of the ultrasonic transducer may be simplified significantly if the housing is implemented in at least two parts. Correspondingly, the housing has at least two housing parts. These housing parts are preferably implemented completely separately and accordingly may preferably be manufactured and/or handled completely independently of one another.

At least one first housing part is provided, which at least partially encloses the transducer core. For example, the housing part may entirely or partially enclose an adjusting body of the transducer core and/or the electroacoustic transducer element. The first housing part may accordingly be implemented, for example, as ring-shaped or tubular, for example, having a round or polygonal cross section. An internal diameter of this housing part may precisely match the external diameter of the transducer core, or an intermediate space may be provided between the housing part and the transducer core, as explained in greater detail below.

The first housing part encloses the transducer core in such a way that a rear side of the electroacoustic transducer element, which faces away from the fluid medium, is accessible. The term accessible is to be understood in the scope of the present invention as a configuration in which the first housing part has at least one opening on the rear side, for example, an opening having a greater opening width than the transducer core, through which the rear side of the electroacoustic transducer element may be accessed, for example, for contacting the electroacoustic transducer element. The opening and/or the transducer element may be implemented in particular in such a way that the transducer core may be introduced through the opening in the first housing part into the first housing part and/or removed therefrom. For example, this rear side of the electroacoustic transducer element may be aligned flush with the rear side of the first housing part or even protrude beyond this first housing part, so that it is accessible for electrical contacting, for example. Alternatively, the first housing part may also protrude slightly on the rear side, so that the rear side of the electroacoustic transducer element is slightly offset into the interior of the housing in relation to the rear side of the first housing part, the rear side of the electroacoustic transducer element still being accessible for electrical contacting, however.

Furthermore, at least one second housing part is provided, which is connected to the first housing part, for example, via an integral and/or force-fitted and/or form-locked connection. This second housing part is implemented and situated in such a way that it essentially terminates the ultrasonic transducer on its side, which faces away from the fluid medium.

However, here, a termination does not mean a hermetic termination, but rather a definition of the outer form of the ultrasonic transducer on the side, which faces away from the fluid medium and/or a mechanical stabilization of components of the ultrasonic transducer accommodated in the housing. Furthermore, at least partial protection from external influences may be ensured. "Essentially" in this regard may be understood as a termination in which at least small openings, for example, for feedthroughs or as a compensation opening with respect to thermal expansion of parts of the transducer (e.g., a damping element), may also be tolerated. "Essentially terminated" may therefore be understood in particular as an embodiment of the second housing part on the side, which faces away from the fluid medium in which the transducer interior, for example, the electroacoustic transducer element and/or the entire transducer core and/or a decoupling element and/or a damping element, may be held in the interior of the housing by the second housing part, so that these components may not be removed from the housing. In particular, the second housing part may provide a rear-side support, on which one or multiple of the elements transducer core, electroacoustic transducer element, decoupling element, damping element, damping and/or decoupling material, or also other elements which are situated in the interior of the housing may be supported. Thus, for example, the second housing part may include at least one supporting element on its side, which faces away from the fluid medium, for example, an inwardly protruding collar, on which one or multiple of the mentioned elements of the housing interior may be supported, so that, for example, a pressure of the fluid medium may be absorbed. For example, it may be ensured in this way that a sealing film on the side of the ultrasonic transducer, which faces toward the fluid medium, is pressed inward as little as possible in the event of a compression load. If at least one rear-side opening is provided in the second housing part, it is also not to be selected as excessively small, however, since the supporting effect is always improved in this case, but thermally induced expansions of the transducer interior, for example of a damping molding compound, would load the optional sealing film all the more. Depending on the hardness, coefficient of thermal expansion, and filling volume, an appropriate compromise for the ideal opening size of the second housing part may be found in practice.

As described above, the first housing part may surround the transducer core in a ring-shaped manner in particular. The first housing part may accordingly be implemented entirely or partially as a ring and/or as a ring-shaped sleeve. For example, the first housing part may have a front surface, in particular a circular front surface, which faces toward the fluid medium. An emission surface of the transducer core, i.e., a surface via which acoustic signals may be delivered from the transducer core to the fluid medium and/or via which acoustic signals may be absorbed from the fluid medium by the transducer core, may be surrounded by this front surface in a ring-shaped manner. For example, the emission surface may be situated in one plane together with this front surface of the first housing part. Such an embodiment is particularly preferred if, as explained in greater detail below, at least one sealing film is provided, which shields and/or seals a housing interior of the ultrasonic transducer against influences from the fluid medium, for example, chemical influences and/or pressure influences. Such a sealing film may be glued or connected in another way, for example, to the front surface of the first housing part and/or to the emission surface.

The electroacoustic transducer element may in particular be aligned flush with the first housing part or protrude beyond the first housing part on the side, which faces away from the fluid medium. This embodiment is particularly advantageous to ensure simple electrical contacting of the electroacoustic transducer element.

The second housing part may be implemented in particular in the form of a pot. In this case, the second housing part, for example, may be put over the first housing part from the side, which faces away from the fluid medium. The first housing part and the second housing part may be connected to one another with the aid of an integral connection process, for example, in particular a welding process. In particular in the case of plastic materials, but also in the case of other materials, ultrasonic welding is recommended in particular. Alternatively or additionally, however, other connection technologies may also be used, for example, force-fitting and/or form-locking and/or integral connection technologies, for example, by laser welding, gluing, or by clipping the second housing part onto the first housing part or vice versa.

Furthermore, the ultrasonic transducer may include at least one contact bridge for electrically contacting the electroacoustic transducer element. For example, the contact bridge may include one, two, or more electrical contacts for contacting electrodes of the electroacoustic transducer element. The at least one contact bridge may be implemented as essentially dimensionally stable, for example, i.e., in such a way that it does not deform or only deforms insignificantly at least under the influence of its intrinsic weight force. The contact bridge may be manufactured from a metallic material in particular. The contact bridge may protrude through the second housing part into an inner chamber of the ultrasonic transducer and may be electrically connected therein to the electroacoustic transducer element. This electrical connection between contact bridge and electroacoustic transducer element may be performed, for example, by directly contacting the electroacoustic transducer element via the contact bridge. Alternatively or additionally, however, other connection technologies may also be used, for example, wire bond technologies. Such bonding technologies may be technically implemented in a particularly simple way, since an access to the electroacoustic transducer element is made easier by the two-part or multipart embodiment of the housing. The contact bridge may be connected to the first housing part in particular. The contact bridge may be spatially fixed in this way in particular. This connection may include a form-locked and/or force-fitted connection, for example. For example, the contact bridge may include one or multiple connection elements, for example clips, with the aid of which it is possible to plug and/or clip the contact bridge onto the first housing part.

The contact bridge may fulfill other tasks in addition to electrical contacting of the electroacoustic transducer element. Thus, for example, it may be implemented at least partially as an electromagnetic shield, for example. The contact bridge may accordingly at least partially enclose the electroacoustic transducer element, for example.

As explained above, the transducer core may include additional elements in the at least one electroacoustic transducer element. For example, the transducer core may include at least one adjusting body, for example, according to the above-described related art. This adjusting body may improve an acoustic coupling between the electroacoustic transducer element and the fluid medium. The first housing part may at least partially surround the adjusting body, for example, enclose it in a ring-shaped manner.

The first housing part and the second housing part may be manufactured, as described above, entirely or partially from a metallic material and/or a plastic material and/or from other materials. Materials which have good intrinsic damping and simultaneously the possibility for also manufacturing filigree structures are particularly preferred. Thus, for example, liquid crystal polymers (LCP) may be used. Alternatively or additionally, other plastics may also be used, for example, PPA (polyphthalamide), PBT (polybutylene terephthalate), and/or PEEK (polyether ether ketone), and/or other plastics. These plastic materials may be implemented as unfilled or also filled, for example, having a filling made of glass fibers, ceramic, carbon, or similar materials.

The first housing part may have an opening, which faces toward the fluid medium in particular. For example, the first housing part, as described above, may have a front surface, for example, a ring-shaped front surface, which encircles the opening. The emission surface of the transducer core may be situated inside this opening. The opening may be closed off by at least one sealing film. The sealing film may be connected, for example, to the first housing part, the front surface, for example.

In particular, at least one housing inner chamber may be provided inside the ultrasonic transducer. This housing inner chamber may be at least partially delimited by the second housing part, for example. This housing inner chamber may be at least partially filled with a filler and/or damping material in particular, for example, a damping molding compound. Silicone is advisable for this purpose, for example.

The damping material may in particular be directly connected to the transducer core, for example, the electroacoustic transducer element, and may be configured to provide the most rapid possible damping after an excitation of the transducer core. Furthermore, the filler and/or damping material may be configured to dissipate pressure forces exerted by the fluid medium on the transducer via the transducer core and the filler and/or damping material on the rear side onto the second housing part.

In addition to the ultrasonic transducer in one or multiple of the above-described embodiments, a method for manufacturing an ultrasonic transducer for use in a fluid medium is also proposed. The method may be used in particular for manufacturing an ultrasonic transducer in one or multiple of the above-described embodiments; however, other types of ultrasonic transducers are also fundamentally manufacturable with the aid of the proposed method. The method includes the steps described hereafter, which do not necessarily have to be carried out in the described sequence. Individual method steps may also be carried out simultaneously and/or overlapping in time. Furthermore, individual or multiple method steps may be carried out repeatedly.

In the method, a transducer core is produced, which includes at least one electroacoustic transducer element. Furthermore, in another method step, at least one first housing part is provided in such a way that the first housing part at least partially encloses the transducer core. At this point in time, the transducer core may already be completely implemented; however, it may also be implemented only partially, for example, in that at this point in time only an adjusting body of the transducer core is provided, which is at least partially enclosed by the first housing part. The first housing part is implemented in such a way and is provided in such a way that a rear side of the electroacoustic transducer element, which faces away from the fluid medium, is accessible, for example, for an electrical contacting process. In another method step, at least one second housing part is provided. This second housing part is connected to the first housing part in such a way that the ultrasonic transducer is essentially terminated on its side, which faces away from the fluid medium, by the second housing part.

The manufacturing method may be designed particularly simply in such a way that at least one sealing film, for example, of the above-described type, is used. For example, this may be a plastic film, for example, as explained in greater detail below, a polyimide film or another film material. However, metallic films are also fundamentally possible. The method may be implemented in such a way that the first housing part and the transducer core or a part of the transducer core, for example an adjusting body, are applied to the sealing film. In particular, they may be connected to the sealing film, for example, by a gluing process and/or another type of integral connection process. An intermediate space between the transducer core or the part of the transducer core and the first housing part is at least partially filled up by at least one damping and/or decoupling material. For example, this damping and/or decoupling material may include a plastic material, in particular a liquid silicone rubber (LSR). The filling up may take place with the aid of a molding process in particular.

Prior to connecting the first housing part and the second housing part, a contact bridge for contacting the electroacoustic transducer element may be connected to the first housing part in particular. This connection may include a form-locked and/or force-fitted connection in particular, as already explained above. The contact bridge may have multiple coherent electrical contacts in particular, the electrical contacts being able to be disconnected from one another after connecting of the contact bridge to the first housing part, for example, after applying of the second housing part to the first housing part.

The proposed ultrasonic transducer and the proposed method have numerous advantages over known ultrasonic transducers and known manufacturing methods. Thus, a foundation is formed for a cost-effective ultrasonic transducer, which is manufacturable in mass production, for example, an air ultrasonic transducer, as may be used for gas flow measurement in the automotive field, for example. An ultrasonic transducer may be used as an ultrasonic flow meter on the pressure side of turbocharged internal combustion engines, for example.

The ultrasonic transducer may be constructed simply and cost-effectively. Thus, the ultrasonic transducer may be manufactured on the basis of a piezoceramic, optionally having an impedance adjustment layer, having a housing in the form of a two-part sleeve, for example. The first housing part may be implemented as the front-side part of the sleeve and may be connected to the adjustment layer. This connection may occur via at least one decoupling element and/or at least one sealing film and/or a coating and/or a combination of these elements, for example. The first housing part, for example the front-side part of the entire sleeve, may be implemented as flat in such a way that the rear side of the piezo is located approximately in one plane together with the rear sleeve edge. The piezo may accordingly be well accessible during the installation, gluing, and contacting processes. The second housing part may in particular be implemented as the rear-side sleeve part. This second housing part may be implemented as a deeper sleeve part than the first housing part. The second housing part may accordingly accommodate a damping and/or a decoupling and/or a supporting material as described above, for example a molding material.

Good accessibility to the piezo rear side is ensured by the at least two-part embodiment of the housing, for example, with the aid of the embodiment of the two-part sleeve, preferably having a relatively flat front part. An advantageous manufacturing sequence may be implemented in this way. The present invention allows more degrees of freedom of the design as a whole, for example, with respect to the selection of the contacting technology. Finally, special requirements for the ultrasonic transducer may be met in this way, for example, requirements of the automotive field, in particular engine attachment conditions.

DETAILED DESCRIPTION OF THE INVENTION

Figure 1:
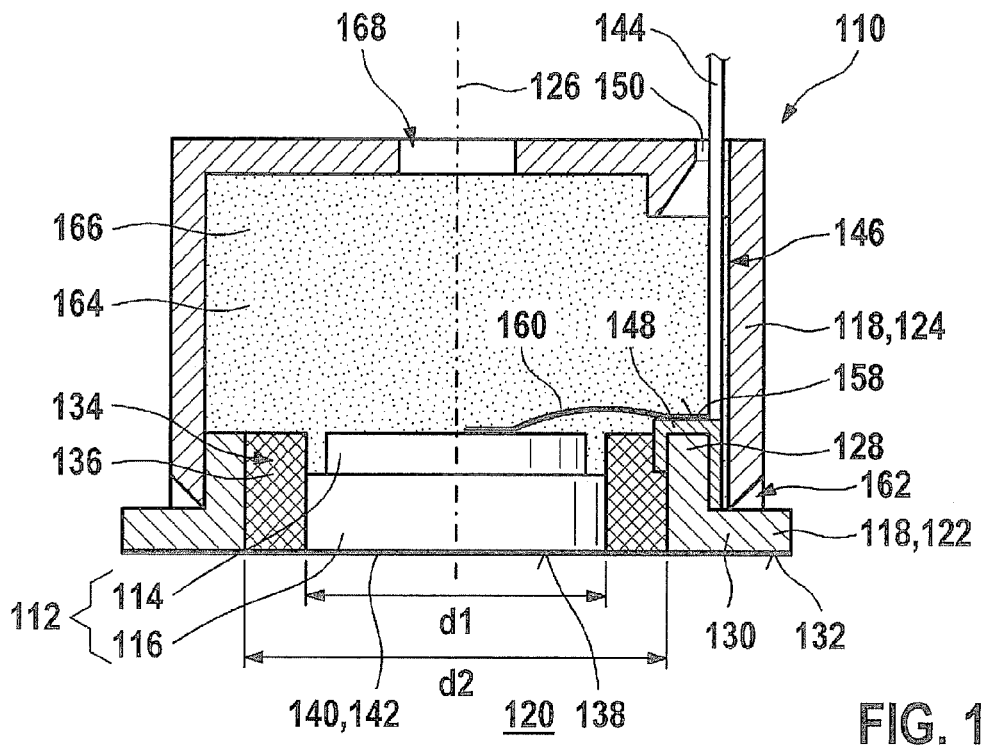
FIG. 1 shows a sectional view of an exemplary embodiment of an ultrasonic transducer according to the present invention.
Figure 2:
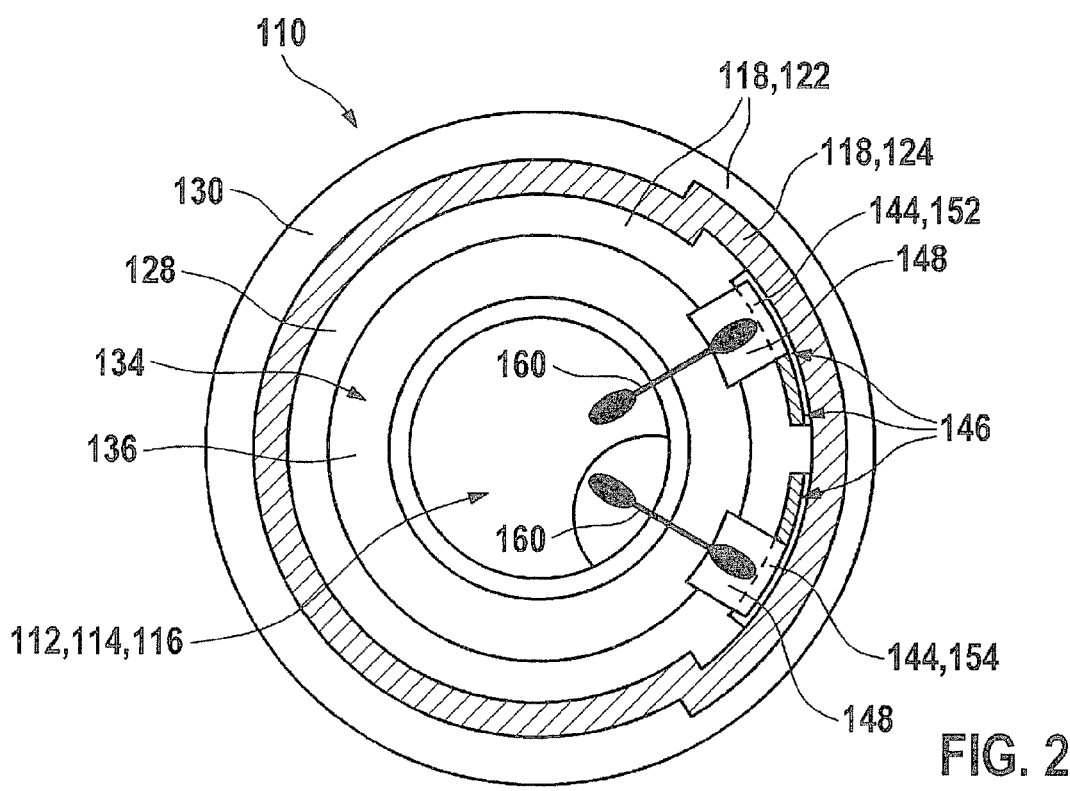
FIG. 2 shows a sectional view of the exemplary embodiment in FIG. 1 having its sectional plane perpendicular to the section plane in FIG. 1.

One possible exemplary embodiment of an ultrasonic transducer 110 according to the present invention is shown in FIGS. 1 and 2. FIG. 1 shows a sectional view from the side, while in contrast FIG. 2 shows a sectional view perpendicular to the sectional plane in FIG. 1 in the top view. Ultrasonic transducer 110 includes a transducer core 112, which in turn includes an electroacoustic transducer element 114 and an adjusting body 116. Adjusting body 116 may be implemented, for example, as a $\lambda/4$ impedance adjustment layer. Electroacoustic transducer element 114 may be implemented, for example, as a piezoelement and may be connected directly or via at least one intermediate layer (for example, an intermediate layer to compensate for thermomechanical tensions) to adjusting body 116. In the illustrated exemplary embodiment, adjusting body 116 has a slightly greater diameter $d_1$ than electroacoustic transducer element 114. For example, entire transducer core 112 may therefore have diameter $d_1$ as a whole, for example, a diameter of 8 mm.

Transducer core 112 is introduced into a housing 118, which is implemented in two parts in the illustrated exemplary embodiment. More than two parts may also fundamentally be provided. Housing 118 accordingly includes a front-side housing part 122, which faces toward a fluid medium 120 (see FIG. 1) in use, and a rear-side second housing part 124, which faces away from fluid medium 120. First housing part 122, which is also referred to hereafter as the first housing sleeve or the front-side sleeve, may be implemented as an essentially cylinder-symmetrical sleeve, for example. As an example, in the illustrated exemplary embodiment, first housing part 122 has an angular design in a section view and has an axial part 128 extending in parallel to an axis 126 and a radial part 130 extending essentially perpendicularly to axis 126. Radial part 130 has a front surface 132, which faces toward fluid medium 120. This front surface 132 is implemented in the form of a circular ring, for example. It has an internal diameter $d_2$ of 12 mm, for example. Accordingly, an intermediate space 134 may be designed between transducer core 112 and first housing part 122, which at least partially surrounds the transducer core. This intermediate space 134 may be implemented in the present case essentially in the form of a cylindrical sleeve, for example, having a thickness of 1 mm, for example. Intermediate space 134 may be entirely or partially filled up using a decoupling element 136, for example, as shown in the exemplary embodiment in FIGS. 1 and 2, which does ensure good mechanical fixation of transducer core 112 in housing 118, but at least partially damps a structure-borne noise transmission between housing 118 and transducer core 112. For example, a molding material may be used as the material for decoupling element 136, for example a liquid silicone rubber (LSR).

Transducer core 112 has an emission surface 138 on its side, which faces toward fluid medium 120. In the illustrated exemplary embodiment, this emission surface is situated in one plane together with front surface 132 of first housing part 122. The side of decoupling element 136, which faces toward fluid medium 120, preferably also does not protrude beyond this common plane of surfaces 132 and 138. Ultrasonic transducer 110 may be sealed to fluid medium 120 via at least one sealing element 140, for example a sealing film 142. Alternatively or additionally, other types of sealing elements 140 also come into consideration, for example coatings. The sealing film may, for example, be connected over a large area to emission surface 138 and/or front surface 132, for example, by gluing.

On the rear side, i.e., on the side which faces away from fluid medium 120, first housing part 122 is implemented as comparatively short, so that in the illustrated exemplary embodiment, the rear side of transducer core 112 is aligned flush with the rear side of first housing part 122 or even protrudes beyond it. Electroacoustic transducer element 114 is accordingly preferably freely accessible from the rear side.

Electroacoustic transducer element 114 is contacted via a contact bridge 144. This contact bridge 144 is guided, for example, in a radial expansion 146 of second housing part 124, which is otherwise implemented as essentially cylindrical, for example as pot-shaped. Contact bridge 144 is guided outward at its upper end through an opening 150 in second housing part 124 and preferably has connecting elements 148 on its lower end for connecting to first housing part 122. These connection elements 148 are implemented in the form of clips or hooks in the illustrated exemplary embodiment, as is apparent from FIG. 1, for example, and may be put and/or clamped over the rear end of axial part 128 of first housing part 122. A form-locked and/or force-fitted connection may, for example, be achieved in this way.

Figure 3:
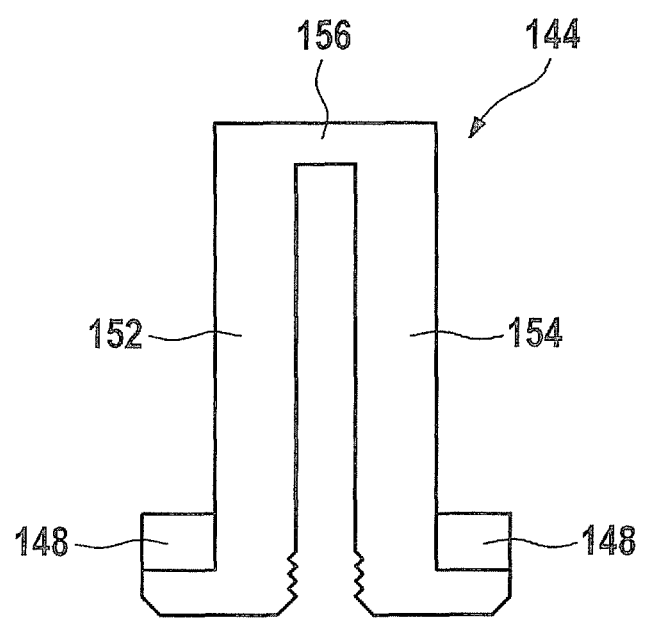
FIG. 3 shows an exemplary embodiment of a contact bridge.

Contact bridge 144 is shown as an example in FIG. 3. It is accordingly apparent that contact bridge 144 has two electrical contacts 152, 154 in the illustrated exemplary embodiment, which may be connected to one another at their upper end by a web 156, for example. This web 156 may be removed after assembly of ultrasonic transducer 110, as explained in greater detail below. Connection elements 148 may protrude laterally, for example, by 2.2 mm, beyond electrical contacts 152, 154, which extend essentially axially. Electrical contacts 152, 154 may also have a width of 2.2 mm, for example, and may be spaced apart by 1.4 mm, for example. Electrical contacts 152, 154 may provide contacting surfaces 158, as is apparent from FIG. 1, for example. A contacting 160 to corresponding contacts of electroacoustic transducer element 114 may be guided via these contacting surfaces 158, for example, by wire bonding, for example. Since the rear side of transducer core 112 is also comparatively freely accessible when transducer core 112 is introduced into first housing part 122 and before second housing part 124 is applied, such contacting is also easily possible by application of wires, for example, or with the aid of other bonding technologies or clamping technologies or other contacting technologies.

After this contacting, second housing part 124, which is pot-shaped, for example, is applied to first housing part 122 and connected thereto, for example by ultrasonic welding. The connection is identified by reference numeral 162 in FIG. 1. An inner chamber 164 is thus formed on the side of transducer core 112, which faces away from fluid medium 120. This inner chamber 164 may be implemented as voluminous, for example, so that it may be completely or partially filled up using at least one filler and/or damping material 166, for example, a damping molding compound, for example. For this purpose, first housing part 122 may include one or multiple openings 168, for example, which may subsequently be closed off or which may also remain in housing 118.

In the illustrated exemplary embodiment according to FIGS. 1 and 2, ultrasonic transducer 110 is thus implemented having a two-part housing 118, for example, a two-part sleeve. A transducer front points downward, toward fluid medium 120 in FIG. 1. A corresponding front-side sleeve part may be implemented as ring-shaped, for example. To manufacture ultrasonic transducer 110 according to FIGS. 1 and 2, front surface 132 of first housing part 122 may be glued onto sealing film 142, for example. Adjusting body 116 may also be glued onto this sealing film 142, so that these elements are fixed. For example, polyimide film (for example, Kapton) may be used as sealing film 142. Decoupling element 136 may be injected and/or embedded in an injection mold as the acoustic decoupling, for example, an LSR material. Electroacoustic transducer element 114 may subsequently be glued on, and connection elements 148, for example the contact pins, of contact bridge 144 may be clipped on axial part 128. As shown in FIGS. 1 and 2, a coherent contact bridge 144 may be used. However, individual contact pins may also alternatively or additionally be used. For example, contact bridge 144 may be opened after the assembly of ultrasonic transducer 110. Contacting 160 may subsequently be applied. For example, copper wires or strips may be fastened via thermocompression welding on the piezoelectrodes and/or contacting surfaces 158, for example the contact lands of the contact pins, for example of contact bridge 144. Alternatively, at least a part of contact bridge 144 may be fastened directly, for example by welding, on the piezoelectrodes and/or contacting surfaces 158. The rear-side sleeve part in the form of second housing part 124 may subsequently be put on and may be connected to first housing part 122, for example the sleeve ring, in particular by ultrasonic welding. A damping molding compound and/or another filler or damping material 166 may subsequently be filled in and cured. Rear-side opening 168 may be used not only for filling in filler or damping material 166, but rather may also allow a compensation for thermal expansions of the damping molding compound within the sensor operating range. On the other hand, this opening 168 is only to be dimensioned as sufficiently large that the transducer interior, i.e., inner chamber 164, may still be sufficiently supported to the rear on the sleeve in the event of counter pressure of fluid medium 120 to be measured, for example, air. The size of opening 168 and/or its geometric embodiment may be implemented for this purpose as a function of the filling volume or the filling geometry and the hardness and the coefficients of expansion of the participating materials in such a way that the emission surface, which faces toward the fluid medium, moves as little as possible both in the event of compression load and also in the event of thermal load.

Ultrasonic transducer 110 shown in FIGS. 1 and 2 only shows one of multiple exemplary embodiments. The exemplary embodiment, and also other exemplary embodiments of the present invention, may be advantageously refined and/or altered in various ways. Thus, for example, an internal decoupling may be provided, which offers a well-defined, hard, and easily sealable mechanical interface to the outside. The material of housing 118 may preferably be manufactured from plastic, since plastic has a particularly good decoupling property. Structure-borne noise components, which are transmitted, for example, via damping material 166, decoupling element 136, or sealing film 142, for example, are sufficiently damped because of the sound damping of the plastic. A liquid crystal polymer (LCP) is particularly suitable, since it is particularly suitable for manufacturing filigree structures and it simultaneously has good intrinsic damping. Other materials are, for example, PPA, PBT, PEEK, or other plastics. The plastic materials may be used in filled or unfilled form, for example, having a filler made of glass fibers, ceramic, carbon, or similar materials. Furthermore, metal and/or a composite material may alternatively or additionally be selected as the material for housing 118 and/or housing parts 122, 124. For example, metal as the sleeve material and/or metal parts inlaid in plastic allow EMC shielding. However, metal tends to have rather long-lasting natural vibrations, which could impair the decoupling properties. In the case of plastic as the sleeve material or as the material of housing 118, contact bridge 144 may also be divided into three instead of only two segments or electrical contacts 152, for example, of which two segments are used for the piezocontacting, for example, and the third segment may represent a shield in the form of a ring or partial ring for electroacoustic transducer element 114 and/or other parts of ultrasonic transducer 110.

As described above, polyimide (for example, Kapton) may come into consideration as the material for sealing film 142, for example. Other alternatively or additionally usable materials are, for example, fluorinated hydrocarbons, such as Teflon and/or PEEK, other types of thermoplastic or duroplastic materials, or also coatings which are not applied as a film, for example, parylenes, lacquers, or similar materials.

Alternatively or additionally to the planar gluing of sealing film 142 to first housing part 122, other connection technologies also come into consideration. Furthermore, the film edge of sealing film 142 may also still be sealed separately. This may be performed simultaneously with the gluing of ultrasonic transducer 110 in a higher-level sensor housing, for example, which is not shown in the figures. For example, multiple such ultrasonic transducers 110 may also be situated in such a higher-order sensor housing, as is shown in the above-cited related art and/or in published German patent application document DE 10 2004 061404 A1. The sensor systems described therein may also be implemented using an ultrasonic transducer 110 according to the present invention.

Sealing film 142 may be glued onto the sleeve ring of first housing part 122 and onto adjusting body 116 in a separate processing step. However, a connection between sealing film 142 and first housing part 122 and/or adjusting body 116 may also additionally or alternatively be produced in another way, for example, in a step including the introduction of decoupling element 136, for example in an injection mold, for example an LSR mold. Alternatively or additionally, the connection may also be performed shortly before or after the LSR process and/or another injection-molding process for introducing decoupling element 136, for example, by the same contact pressure which also closes or seals the mold, for example the LSR mold.

Alternatively or additionally, other types of decoupling elements 136 may also be used. Decoupling element 136 may thus also be implemented and/or installed entirely or partially as a molded part. One advantage of this procedure could be a lower strain on the adjustment layer material. However, a fundamentally higher tolerance because of the softer consistency is disadvantageous in this case. Another variant, which may be used alternatively or additionally, is extrusion coating of the material of decoupling element 136, for example the LSR, only on first housing part 122 and optionally sealing film 142, while adjusting body 116 is applied, for example glued on, in a separate processing step.

Alternatively to the LSR process, a damping and/or decoupling material may also be introduced with the aid of a casting technology. Other materials may also be used instead of silicone. Decoupling element 136 may also be omitted as a separate material and/or may be entirely or partially combined with damping material 166. For example, a single molding material may be used, which represents a compromise between damping and decoupling. This may be a silicone material, for example. Flexibilized epoxides having additional fillers are also conceivable as the basic material, for example.

Further modifications and/or refinements relate to adjusting body 116. For example, it may be implemented according to the above-described related art. In particular, adjusting body 116 may be made of epoxide, filled with hollow glass beads, and/or porous sintered polyimide, for example, polyimide of the type Vespel from DuPont or other materials and/or also gradient materials, whose acoustic impedance or whose impedance curve is selected in such a way that a favorable coupling is provided between electroacoustic transducer element 114 and fluid element 120. One or multiple additional layers may be placed between electroacoustic transducer element 114 and adjusting body 116, which protect electroacoustic transducer element 114, for example the piezo, from pretensions in that they have coefficients of expansion close to the piezomaterial, for example (i.e., in the magnitude of 10 ppm/K or less, for example), and have a sufficient thickness. This at least one layer may simultaneously be used for the purpose of sealing open pores of adjusting body 116 against an adhesive, using which electroacoustic transducer element 114 is fastened. This at least one optional additional layer may be glued or applied by a molding method, for example, and/or may be part of adjusting body 116, for example the adjustment layer, in particular having different thermal/acoustic properties.

The diameter of electroacoustic transducer element 114 may be selected in such a way that essentially the planar resonance is exploited for the ultrasound generation and/or ultrasound detection. The thickness of electroacoustic transducer element 114 may represent a compromise. The thinner the piezo is selected, for example, the more flexible it is, which makes it more stable with respect to thermal shocks. On the other hand, an excessively thin piezo executes excessively strong bending oscillations, which may result together with adjusting body 116 in an excessively strong temperature sensitivity of ultrasonic transducer 110. The connection between electroacoustic transducer element 114 and adjusting body 116 or a compensation layer may also be performed without a separate adhesive, for example, in that a piezoelement is embedded directly into adjusting body 116 and/or at least one intermediate body. The connection between electroacoustic transducer element 114 and adjusting body 116 and/or the optional compensation layer may be flexibilized so that the piezofunction is not impaired by the thermal change of adjusting body 116 or the compensation layer or by temperature shock. On the other hand, the connection is preferably selected as sufficiently hard that a sufficient acoustic coupling is present. An epoxy-based material may typically be used for this purpose.

The electrical connection between the electrodes of electroacoustic transducer element 114, for example, the piezo, and the contact bridge, which may generally comprise one or multiple contact pins, may be produced in various ways. For example, as explained above, a connection may be performed using wires, strips, films, or also litz wires. Instead of the mentioned thermo-compression welding, other technologies also fundamentally come into consideration as the contacting. For example, conductive adhesives, solders, or wire bonds suggest themselves. The contact points or also the entire connection between the electroacoustic transducer element and contact bridge 144 and/or individual contact pins of this contact bridge 144 may be covered using a hard protective compound, for example a glob top compound and/or using soft silicone gel, in order to protect them, for example from corrosion. The contact pins may fundamentally also be fixedly connected to one of the housing parts of housing 118, for example, as an inlet part or as a lead frame and/or as extrusion-coated parts.

What is claimed is:

1. An ultrasonic transducer for use in a fluid medium, comprising:
   at least one transducer core including at least one electroacoustic transducer element;
   at least one housing having at least two housing parts, wherein at least one first housing part at least partially encloses the transducer core such that a rear side of the electroacoustic transducer element which faces away from the fluid medium is accessible, and wherein at least one second housing part is connected to the first housing part and terminates the ultrasonic transducer on a side which faces away from the fluid medium; and
   at least one contact bridge electrically contacting the electroacoustic transducer element, wherein the contact bridge protrudes through the second housing part into an inner chamber of the ultrasonic transducer and is electrically connected to the electroacoustic transducer element in the inner chamber, and wherein the contact bridge is connected to the first housing part by at least one of a form-locked and a force-fitted connection.

2. The ultrasonic transducer as recited in claim 1, wherein the first housing part surrounds the transducer core in a ring-shaped manner.

3. The ultrasonic transducer as recited in claim 2, wherein the electroacoustic transducer element is one of (i) aligned flush with the first housing part or (ii) protrudes beyond the first housing part on the side which faces away from the fluid medium.

4. The ultrasonic transducer as recited in claim 2, wherein the second housing part is pot-shaped element and is put over the first housing part from the side which faces away from the fluid medium.

5. The ultrasonic transducer as recited in claim 2, wherein the first housing part and the second housing part are connected to one another by welding.

6. The ultrasonic transducer as recited in claim 1, wherein the contact bridge at least partially encloses the electroacoustic transducer element and provides an electromagnetic shield.

7. The ultrasonic transducer as recited in claim 6, wherein the first housing part and the second housing part are plastic material.

8. A method for manufacturing an ultrasonic transducer for use in a fluid medium, comprising:
   producing a transducer core including at least one electroacoustic transducer element;
   providing at least one first housing part which at least partially encloses the transducer core such that a rear side of the electroacoustic transducer element which faces away from the fluid medium is accessible;
   providing at least one second housing part;
   providing at least one contact bridge electrically contacting the electroacoustic transducer element, wherein the contact bridge protrudes through the at least one second housing part into an inner chamber of the ultrasonic transducer and is electrically connected to the electroacoustic transducer element in the inner chamber, and wherein the contact bridge is connected to the at least one first housing part by at least one of a form-locked and a force-fitted connection; and
   connecting the first housing part and the second housing part in such a way that the ultrasonic transducer is terminated by the second housing part on a side which faces away from the fluid medium.

9. The method as recited in claim 8, wherein the first housing part and at least an adjusting body element of the transducer core are applied onto a sealing film, and wherein an intermediate space between the at least the adjusting body element of the transducer core and the first housing part is at least partially filled by at least one of a damping material and a decoupling material.

10. The method as recited in claim 8, wherein before the connection of the first housing part and the second housing part, the contact bridge for contacting the electroacoustic transducer element is connected to the first housing part.

* * * * *